United States Patent [19]

Anderson et al.

[11] Patent Number: 6,096,918
[45] Date of Patent: Aug. 1, 2000

[54] ARYL-ACRYLIC ACID ESTERS

[75] Inventors: Denise Anderson, Zürich; Georg Frater, Winterthur, both of Switzerland

[73] Assignee: Givaudan Roure (International) SA, Geneve, Switzerland

[21] Appl. No.: 09/249,384

[22] Filed: Feb. 12, 1999

[30] Foreign Application Priority Data

Feb. 13, 1998 [EP] European Pat. Off. .............. 98810114

[51] Int. Cl.$^7$ .................................................. C07C 69/76
[52] U.S. Cl. .......................... 560/104; 558/401; 562/495
[58] Field of Search ........................ 562/495; 560/104, 560/105, 238; 548/356.1, 268.6, 364.4, 124, 126, 217, 241

[56] References Cited

U.S. PATENT DOCUMENTS 5,334,750  8/1994  Kaufmann et al. ..................... 560/104
5,649,979  7/1997  Paget et al. ................................. 8/137
5,726,345  3/1998  Paget et al. ............................. 560/238

FOREIGN PATENT DOCUMENTS 2736354   7/1995  France .
WO 95/04809  2/1995  WIPO .

OTHER PUBLICATIONS

Bartlett, et al., *Heterocycles,* vol. 11, pp. 419–435 (1978).
Bunce, et al., *Org. Prep. Proc.,* vol. 29(3), p. 293 (1997).

*Primary Examiner*—Ardin H. Marschel
*Assistant Examiner*—Sherif Kafafi
*Attorney, Agent, or Firm*—Mark E. Waddell; Stephen M. Haracz; Bryan Cave LLP

[57] ABSTRACT

The acrylic acid esters of Formula I are useful for the delivery of organoleptic compounds, especially for flavors, fragrances, masking agents and antimicrobial compounds. They can also deliver fluorescent whitening agents.

18 Claims, No Drawings

ARYL-ACRYLIC ACID ESTERS

FIELD OF INVENTION

The present invention relates to 3-(2-substituted aryl)-acrylic acid esters, especially 3-(2-hydroxyaryl)-acrylic acid esters and 3-(2-aminoaryl)-acrylic acid esters. These compounds are useful as precursors for organoleptic compounds, such as for example, flavors, fragrances and masking agents, antimicrobial compounds and fluorescent whitening agents.

BACKGROUND OF THE INVENTION

A principal strategy currently employed for imparting odors, such as fragrance, to consumer products is to admix the fragrance directly into the product. There are, however, several drawbacks to this strategy. For example, the fragrance material can be too volatile and/or too soluble, resulting in fragrance loss during manufacturing, storage, and use. In addition, many fragrance materials are also unstable over time which, again, results in loss during storage.

In many consumer products it is desirable for the fragrance to be released slowly over time. Microencapsulation and inclusion complexes with cyclodextrins have been used to help decrease volatility, improve stability and provide slow-release properties. These methods are, for a number of reasons, often not successful and/or too expensive to be commercially viable, as for example, in the case of cyclodextrins.

Fragrance precursors for scenting fabrics being washed in the presence of a lipase-containing detergent are described in WO 95/04809. The fragrance precursors contained in the detergent and/or in the softener are cleaved by the lipase and a single active compound. In such a situation, an odoriferous alcohol, aldehyde or ketone is produced. In this system, a prolonged scenting effect on the fabric is obtained. However, the need for a lipase-containing detergent is of limited commercial significance. In many parts of the world, detergents do not contain lipase. Other consumers prefer to use so-called 'nonbio' detergents.

Fluorescent whitening agents or brighteners have been added to laundry detergents since the 1950s to help maintain the original brightness of white clothing.

Accordingly, one object of the present invention is to provide new precursors for compounds with different activities. Through these precursors, different activities are imparted to a product by the addition of just one compound of the present invention.

Another object of the invention is to provide new precursor compounds which are stable under transport and storage conditions.

A further object of the present invention is to provide new precursors that supply different active compounds simultaneously or successively.

SUMMARY OF THE INVENTION

The present invention provides compounds of the Formula I

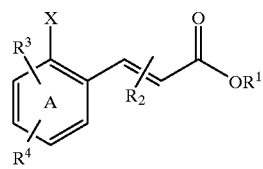

wherein A is a benzene or a naphthalene ring; $R^1$ is, or is selected from saturated, unsaturated, straight, branched, alicyclic and/or aromatic $C_{10}$–$C_{30}$ hydrocarbon residues which can contain heteroatoms and can be substituted by an ionic substituent; $R^2$ in the 2- or 3-position is, or is selected from hydrogen, a straight or branched $C_1$–$C_6$ residue, an optionally substituted aromatic and/or optionally substituted heterocyclic residue; $R^3$ and $R^4$ are, or selected from hydrogen, a straight or branched $C_1$–$C_6$ alkyl, a $C_1$–$C_6$ alkoxy residue, a substituted or condensed heterocyclic residue, —OH, —$NO_2$, —$NH_2$, —N($C_1$–$C_6$ alkyl)$_2$, —N(hydroxyalkyl)$_2$, —$NHCO_2CH_3$ and/or —NH (heterocycle).

In the present invention, $R^2$, $R^3$ and $R^4$ are the same or different. X is, or is selected from —OH and/or $NHR^6$, wherein $R^6$ is, or is selected from hydrogen, a saturated or unsaturated, straight or branched $C_1$–$C_{20}$ hydrocarbon and/or an optionally substituted aromatic or heterocyclic residue; and the acrylic double bond is of the E configuration.

The present invention also provides a method for preparing organoleptic, antimicrobial and fluorescent whitening compositions by incorporating into these precursor compounds of Formula I described above.

DETAILED DESCRIPTION OF THE INVENTION

The present invention provides novel 3-(2-substituted aryl)-acrylic acid esters of the Formula I set forth below:

(I)

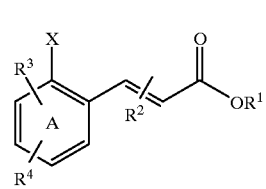

wherein
  A is a benzene or naphthalene ring;
  $R^1$ is a saturated or unsaturated, straight, branched, alicyclic or aromatic $C_{10}$–$C_{30}$ hydrocarbon residue which can contain heteroatoms and can be substituted by an ionic substituent;
  $R^2$ in the 2- or 3-position is hydrogen, a straight or branched $C_1$–$C_6$ residue, an optionally substituted aromatic or an optionally substituted heterocyclic residue;
  $R^3$ and $R^4$ are hydrogen, a straight or branched $C_1$–$C_6$ alkyl or $C_1$–$C_6$ alkoxy residue, a substituted or condensed heterocyclic residue, —OH, —$NO_2$, —$NH_2$, —N($C_1$–$C_6$ alkyl)$_2$, —N(hydroxyalkyl)$_2$, —$NHCO_2CH_3$ or —NH(heterocycle);
  $R^2$, $R^3$ and $R^4$ may be the same or different;
  X is —OH or $NHR^6$, wherein $R^6$ is hydrogen a saturated or unsaturated, straight or branched $C_1$–$C_{20}$ hydrocarbon or an optionally substituted aromatic or heterocyclic residue; and the acrylic double bond is of the E configuration.

In the present invention, Formula I includes all possible enantiomers, diastereomers and all mixtures thereof.

In Formula I, $R^1$ is preferably a saturated or unsaturated, straight or branched $C_{10}$–$C_{30}$ hydrocarbon residue containing one or more O and/or N atoms and/or C(O) groups and/or alkoxy groups or substituted by an ionic substituent of the formula $N(R^5)_3^+$, in which $R^5$ is the residue of a fatty acid or an alkyl group with 1 to 30 carbon atoms are preferred.

In Formula I, $R^2$ is preferably a heterocyclic residue of the formula

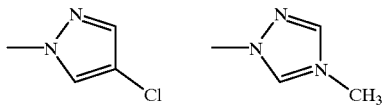

In Formula I, $R^3$ and/or $R^4$ are preferably hydrogen, —N($C_1$–$C_6$ alkyl)$_2$, —NH$_2$, a five membered heterocyclic residue optionally containing N and/or O atoms, substituted by $C_1$–$C_6$ aliphatic and/or aromatic substituents.

In one embodiment of the present invention, $R^1$ is preferably the residue of an olfactory alcohol of the formula $R^1OH$, of the enol form of an olfactory aldehyde of the formula $R^1$ is an optionally substituted alkyl, alkenyl or arylalkyl residue carrying an 1-alkoxy, 1-aryloxy, or 1-arylakoxy residue.

In the present invention, compounds within the scope of Formula I are mostly or nearly odorless at room temperature, atmospheric conditions and about 20 to 100% relative humidity. Under activating conditions, however, compounds of Formula I are cleaved to form active compounds. For example, the residue of Formula Ia when cleaved forms a coumarin of Formula II.

The structures of Formulae Ia and II are set forth below:

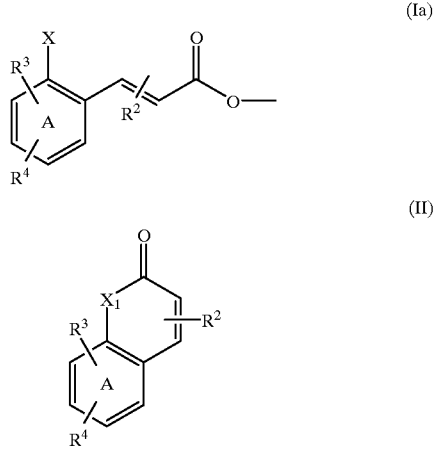

wherein $X^1$ is O or $NR^6$; $R^2$, $R^3$, $R^4$ are defined as set forth above.

In the present invention, the coumarins of Formula II have organoleptic, antimicrobial and/or optical brightening activity. Preferably, coumarins of the present invention have olfactory properties.

In the present invention, when $R^1$ is the residue of an olfactory alcohol or the enol form of an olfactory aldehyde or ketone, upon cleavage two active compounds with the above properties can be obtained. Thus, the compounds of Formula I permit the development of useful consumer products with enhanced organoleptic, antimicrobial and/or optical brightening properties. The organoleptic coumarins, alcohols, aldehydes and ketones obtained from the present compounds are useful, for example, in preparing fragrances, flavors, masking agents and antimicrobial agents.

To form active residues from Formula I and Ia, these compounds are subject to activating conditions that lead to the cleavage of thereof. In the present invention, actinic radiation, such as, UV light, including sunlight can be used to activate the compounds of Formula I. Elevated temperatures also function to activate the compounds of Formula I and Ia. For purposes of the present invention, any activating condition may be used, so long as the desired active ingredients are formed by cleavage of compounds of Formula I and Ia to form the desired residue with the proper activity.

Another embodiment of the present invention is a method for preparing organoleptic, antimicrobial and fluorescent whitening compositions wherein the compounds of Formula I are precursors for these compounds. For purposes of the present invention, organoleptic precursors include, for example, precursors compatible in flavors, fragrances and odor masking agents.

In the present invention, the esters of formula I can act as fragrance precursors in laundry products. They can also act as precursors for odor masking agents in the same products as the fragrance precursors. They also can act as precursors for antimicrobial agents. In addition, they can also act as precursors for fluorescent whitening agents. The fragrance precursors and the precursors for odor masking agents as well as the flavor precursors of the invention may be used individually in an amount effective to enhance or to mask the characteristic odor or flavor of a material. More commonly, however, the compounds are mixed with other fragrance or flavor components in an amount sufficient to provide the desired odor or flavor characteristics.

Thus, as used herein, an "effective" amount is intended to mean a sufficient quantity of the precursor to obtain the desired effect, i.e., fragrance, odor masking and/or flavoring. Reference is made to the Examples set forth below and to the skill of the art for determining an effective amount of the present inventive compounds in any given situation.

The brightener precursors may also be employed individually in an effective amount where appropriate, and/or mixed with one or more other brightener or colorant substance.

Due to the in situ generation of the active compounds of the present invention, the desired effect is prolonged and the substantivity on different substrates is enhanced. If two active compounds are provided by one ester of the Formula I, they can be generated, depending on the precursor and/or the activating conditions, simultaneously or successively. Further, the precursors of the present invention provide slow release of the active compounds.

Non-limiting examples of alcohols $R^1OH$ generated upon cleavage of compounds of Formula I and constituting the residue $R^1$, include amyl alcohol, hexyl alcohol*, 2-hexyl alcohol*, heptyl alcohol*, octyl alcohol*, nonyl alcohol*, decyl alcohol* undecyl alcohol*, lauryl alcohol*, myristic alcohol, 3-methyl-but-2-en-1-ol*, 3-methyl-1-pentanol, cis-3-hexenol*, cis-4-hexenol*, 3,5,5-trimethyl-hexanol, 3,4,5, 6,6-pentamethylheptan-2-ol*, citronellol*, geraniol*, oct-1-en-3-ol, 2,5,7-trimethyl-octan-3-ol, 2-cis-3,7-dimethyl-2,6-octadien-1-ol, 6-ethyl-3-methyl-5-octen-1-ol*, 3,7-dimethyl-oct-3,6-dienol*, 3,7-dimethyloctanol*, 7-methoxy-3,7-dimethyl-octan-2-ol*, cis-6-nonenol*, 5-ethyl-2-nonanol, 6,8-dimethyl-2-nonanol*, 2,2,8-trimethyl-7(8)-nonene-3-ol, nona-2,6-dien-1-ol, 4-methyl-3-decen-5-ol*, dec-9-en-1-ol, benzylalcohol, 2-methylundecanol, 10-undecen-1-ol, 1-phenyl-ethanol*, 2-phenyl-ethanol*, 2-methyl-3-phenyl-3-propenol, 2-phenyl-propanol*, 3-phenyl-propanol*, 4-phenyl-2-butanol, 2-methyl-5-phenyl-pentanol*, 2-methyl-4-phenyl-pentanol*, 3-methyl-5-phenyl-pentanol*, 2-(2-methylphenyl)-ethanol*, 4-(1-methylethyl)-benzene-methanol, 4-(4-hydroxyphenyl)-butan-2-one*, 2-phenoxy-ethanol*, 4-(1-methylethyl)-2-hydroxy-1-methyl benzene, 2-methoxy-4-methyl-phenol, 4-methyl-phenol, anisic alcohol*, p-tolyl alcohol*, cinnamic alcohol*, vanillin*, ethyl vanillin*, eugenol*, isoeugenol*, thymol, anethol*, decahydro-2-naphthalenol, borneol*, cedrenol*, farnesol*, fenchyl alcohol*, menthol*, 3,7,11-trimethyl-2,6,10-dodecatrien-1-ol, alpha ionol*, tetrahydro ionol*, 2-(1,1-dimethylethyl)cyclohexanol*, 3-(1,1-dimethylethyl) cyclohexanol*, 4-(1,1-dimethylethyl)cyclohexanol*, 4-isopropyl-cyclohexanol, 6,6-dimethyl-bicyclo[3.3.1]hept-2-ene-2-ethanol, 6,6-dimethyl-bicyclo[3.1.1]hept-2-ene-methanol*, p-menth-8-en-3-ol*, 3,3,5-trimethyl-cyclohexanol, 2,4,6-trimethyl-3-cyclohexenyl-methanol*, 4-(1-methylethyl)-cyclohexyl-methanol*, 4-(1,1-dimethylethyl)-cyclohexanol, 2-(1,1-dimethylethyl)-cyclohexanol, 2,2,6-trimethyl-alpha-propyl-cyclohexane propanol*, 5-(2,2,3-trimethyl-3-cyclopentenyl)-3-methylpentan-2-ol*, 3-methyl-5-(2,2,3-trimethylcyclopentyl-3-enyl)pent-4-en-2-ol*, 2-ethyl-4(2,2,3-trimethylcyclopentyl-3-enyl)but-2-en-1-ol*, 4-(5,5,6-trimethylbicyclo[2.2.]hept-2-yl)-cyclohexanol*, 2-(2-methylpropyl)-4-hydroxy-4-methyl-tetrahydropyran*, 2-cyclohexyl-propanol*, 2-(1,1-dimethylethyl)-4-methyl-cyclohexanol*, 1-(2-tert-butyl-cyclohexyloxy)-2-butanol*, 1-(4-isopropyl-cyclohexyl)-ethanol*, 2,6-dimethyl-oct-7-en-2-ol, 2,6-dimethyl-heptan-2-ol and 3,7-dimethyl-octa-1,6-dien-3-ol**.

In the list set forth above, the alcohols identified with an asterisk are preferred embodiments, and the alcohols identified with two asterisks are more preferred.

Non-limiting examples of aldehydes R¹HO generated upon cleavage a compound of Formula I and constituting the residue R¹ thereof include, for example, 2,6,10-trimethylundec-9-enal*, 1,2,3,4,5,6,7,8-octahydro-8,8-dimethyl-2-napthalenecarboxaldehyde tridecanal, 2-[4-(1-methylethyl)phenyl]-ethanal, 2,4-dimethyl-cyclohex-3-ene-1-carbox-aldehyde*, 4-carboxaldehyde-1,3,5-trimethyl-cyclohex-1-ene*, 1-carboxaldehyde-2,4-dimethyl-cyclohex-3-ene*, 1-carboxaldehyde-4-(4-hydroxy-4-methylpentyl)-cyclohex-3-ene*, 3,5,5-trimethyl-hexanal, heptanal*, 2,6-dimethyl-hept-5-enal*, decanal**, dec-9-enal, dec-4-enal, 2-methyldecanal*, undec-10-enal**, undecanal*, dodecanal, 2-methyl-undecanal, tridecanal, octanal**, nonanal*, 3,5,5-trimethylhexanal, undec-9-enal**, 2-phenyl-propanal*, 4-methyl-phenyl-acetaldehyde*, 3,7-dimethyl-octanal*, dihydrofarnesal**, 7-hydroxy-3,7-dimethyl-octanal*, 2,6-dimethyl-oct-5-enal, 2-[4-(1-methylethyl)phenyl]-ethanal*, 3-(3-isopropyl-phenyl)-butanal**, 2-(3,7-dimethyoct-6-enoxy)-ethanal, 1-carboxaldehyde-4-(4-methyl-3-pentenyl)-cyclohex-3-ene*, 2,3,5,5-tetramethyl-hexanal, longifolic aldehyde, 2-methyl-4-(2,6,6-trimethylcyclohex-2-en-1-yl)-butanal*, 2-methyl-3-(4-tert-butylphenyl)-propanal**, 4-(1,1-dimethyl-ethyl)-benzene-propanal*, 2-[4-(1-methyl-ethyl)-phenyl]-propanal, alpha-methyl-1,3-benzodioxole-5-propanal*, 3,7-dimethyl-oct-6-enal*, 2-methyl-3-(4-isopropylphenyl)-propionaldehyde*, 4-(4-hydroxy-4-methyl-pentyl)-cyclohex-3-en-1-carboxaldehyde**, alpha-methyl-1,3-benzodioxole-5-propanal*, 1-carboxaldehyde-4-(1,1-dimethylethyl)-cyclohexane, 4-(octahydro-4,7-methano-5H-inden-5-ylidene)-butanal and [(3,7-dimethyl-6-octenyl)-oxy]-acetaldehyde**.

In the list set forth above, the aldehydes identified with an asterisk are preferred embodiments, and the alcohols identified with two asterisks are more preferred.

Non-limiting examples of ketones R¹O generated upon cleavage a compound of Formula I and constituting the residue R¹ thereof include, for example, 2-heptyl-cyclopentanone, 2,2,6,10-tetrametyltricyclo-[5.4.0.0(6,10)]-undecan-4-one benzylacetone*, carvone*, 1,2,3,5,6,7-hexahydro-1,1,2,3,3-pentamentyl-4H-inden-4-one*, methyl heptenone*, dimethyl octenone*, 2-(butan-2-yl)-cyclohexanone*, 2-hexyl-cyclopent-2-en-1-one*, 2-(1-methylethyl)-5-methyl-cyclohexanone*, 2-(2-methylethyl)-5-methyl-cyclohexanone*, 3-methyl-cyclopentadecanone, 4-tert-pentyl-cyclohexanone*, 3-oxo-2-pentyl-cyclopentane-acetic acid methyl ester**, 1-(1,2,3,4,5,6,7,8-octahydro-2,3,8,8-tetramethyl-2-naphthalenyl)-ethanone* and 3-methyl-5-propyl-cyclohex-2-en-1-one*.

In the list set forth above, the ketones identified with an asterisk are preferred embodiments, and the alcohols identified with two asterisks are more preferred.

Non-limiting examples of fluorescent whitening coumarins generated upon cleavage a compound of Formula I and constituting the residue R¹ thereof include, for example, 7-(3-methyl-1H-pyrazol-1-yl)-3-phenyl-2H-1-benzopyran-2-one, 7-(4-methyl-5-phenyl-2H-1,2,3-triazol-2-yl)-3-phenyl-2H-1-benzopyran-2-one, 7-(2H-naphtho[1,2-d]triazol-2-yl)-3-phenyl-2H-1-benzo-pyran-2-one, 3-(1H-pyrazol-1-yl)-7-(2H-1,2,3-triazol-2-yl)-2H-1-benzo-pyran-2-one, 7-(dimethylamino)-1-methyl-3-phenyl-2(1H)-quinolinone, 7-(diethylamino)-1-ethyl-3-phenyl-2(1H)-quinolinone, 7-amino-4-methyl-2H-1-benzopyran-2-one, 7-(dimethylamino)-4-methyl-2H-1-benzopyran-2-one, 7-(diethylamino)-4-methyl-2H-1-benzopyran-2-one, 7-hydroxy-4-methyl-2H-1-benzopyran-2-one and 6,7-dihydroxy-2H-1-benzopyran-2-one.

Non-limiting examples of coumarins of Formula II having olfactory properties generated upon cleavage and constituting the respective residue in the compounds of Formula I, include 2H-1-benzopyran, 3-methyl-benzopyran-2-one, 8-(1,1-dimethylethyl)-6-methyl-benzopyrone, 4-methyl-7-ethoxy-coumarin and 6-methyl-2H-1-benzopyran.

The active coumarins, alcohols, aldehydes and ketones which are generated as a result of the desired cleavage of the acrylic acid esters of Formula I by UV-light and/or by elevated temperatures is exemplary only and is not intended to limit the scope of the present invention in any way.

The compounds of Formula I, preferably, may be employed in preparing sustained release odorants and flavors. The compounds of Formula I also are useful as sustained agents which may be employed to mask or attenuate undesirable odors or to provide additional odors not initially present in consumer products including for example, laundry detergents, fabric softeners, fabric softener sheets, toiletries and cosmetics such as sunscreens.

Further applications of the compounds of Formula I include sustained brighteners and antimicrobial agents in the same products. The brighteners are especially useful for wool, rayon and polyamides. These compounds are also useful for flavoring and aromatizing tobacco products, such as for example, cigarettes.

The amount of the compounds of the present invention required to produce the desired, overall effect varies depending upon the particular compounds of Formula I chosen, the product in which it will be used, and the particular effect desired. The examples teach what amounts are suitable for any desired purpose.

For example, depending upon the selection and concentration of the compound chosen, when a compound of Formula I is added either singly or as a mixture to, for example, a laundry product composition at levels ranging from about 0.001 to about 10% by weight, a coumarin and if desired an odoriferous alcohol, aldehyde or ketone in an organoleptically effective amount is released when the product is used. These newly formed odorant(s) serve to enhance the odor of the fragrance. Depending on the compound of Formula I, an antimicrobial agent and/or a brightener can be released.

Depending upon the selection and concentration, addition of the Formula I compounds, either singly or as a mixture, to cigarette tobacco at levels ranging from about 5 ppm to about 50,000 ppm tends to enhance the smoking flavor and/or mask undesirable smoking odors. An important property of these Formula I compounds is that the flavorant or odorant is covalently bound as a non-volatile compound and the flavorant or odorant is released only when the tobacco product is ignited and burns.

Addition of the compounds of Formula I, either separately, or as a mixture, at levels suitably ranging from about 5 ppm to about 50,000 ppm by weight onto the media enclosing the tobacco, serves to incorporate the odorant/flavorant in the side-stream smoke of the tobacco. Air borne flavorants and/or odorants are thus introduced. This newly formed odorant or flavorant enhances and masks the smoking odors, depending upon selection and use levels of the compounds of Formula I.

As is evident from the above compilation of alcohols, aldehydes, ketones and coumarins, a broad range of odorants or flavors or mixtures can be generated from precursors of the invention. While manufacturing compositions, the precursors of the invention may be used according to methods known to the perfumer, such as e.g. from W. A. Poucher, Perfumes, Cosmetics, Soaps, 2, 7th Edition, Chapman and Hall, London 1974 which is hereby incorporated by reference. The fluorescent whitening agents may be added in similar manner.

The following examples are provided to further illustrate methods of preparation of the compounds of the present invention, as well as certain physical properties and uses thereof. These examples are illustrative only and are not intended to limit the scope of the invention in any way.

EXAMPLES

Example 1

(E)-3-(2-Hydroxy-phenyl)-2-methyl-acrylic acid ethyl ester

To a solution of 75.0 g (carbethoxyethylidene)triphenyl phosphorane in 350 ml of toluene, 23.2 g of salicylaldehyde was dropped in at 20° C. while cooling in an ice-bath. After stirring at room temperature for 90 mn., the reaction mixture was diluted with toluene and washed to neutrality with water.

The organic phase was dried, filtered and evaporated to dryness. The resulting yellow oil was purified by chromatography to yield 35.5 g of a colourless solid.

NMR (CDCl$_3$) δ 7.82 (s, 1H), 7.30–6.85 (m, 4H), 6.6 (s, OH), 4.35–4.17 (q, 2H), 2.04 (s, 3H), 1.40–1.28 (t, 3H)

Example 2

(E)-3-(2-Hydroxy-phenyl)-acrylic acid methyl ester

According to the procedure of Example 1, (E)-3-(2-hydroxy-phenyl)-2-methyl-acrylic acid methyl ester was prepared from methyl(triphenyl-phosphoranylidene)acetate and salicylaldehyde.

Example 3

(E)-3-(2-Hydroxy-phenyl)-acrylic acid ethyl ester

According to the procedure of Example 1, (E)-3-(2-hydroxy-phenyl)-2-methyl-acrylic acid methyl ester was prepared from ethyl(triphenyl-phosphoranylidene)acetate and salicylaldehyde.

Example 4

(E)-3(2-Hydroxy-phenyl)-2-methyl-acrylic acid

To a solution of 35.5 g of (E)-3-(2-hydroxy-phenyl)-2-methyl-acrylic acid ethyl ester in 600 ml of ethanol, a solution of 10.66 g of potassium hydroxide in 500 ml of water was dropped in. After refluxing for 5 hours, another 5.0 g of potassium hydroxide was put in and the mixture was refluxed for another 19 hours. Then the reaction mixture was cooled down, diluted with ether and washed to pH 4 with HCl 2N and water. The organic phase was dried, filtered and evaporated to dryness. The resulting colourless crystals were not further purified.

NMR (CDCl$_3$) δ 7.90 (s, 1H), 7.31–6.83 (m, 4H), 2.07 (s, 3H)

Example 5

(E)-3-(2-Hydroxy-phenyl)-2-methyl-acrylic acid 3,7 dimethyl-oct-6-enyl ester

A solution of 6.0 g of (E)-3-(2-hydroxy-phenyl)-2-methyl-acrylic acid, 5.3 g of citronellol and 1 g of p-toluene-sulfonic acid in 150 ml of cyclohexane was refluxed for 6.5 hours using a water separator. Then the reaction mixture was cooled down, diluted with hexane and washed to neutrality with saturated sodium bicarbonate and water. The organic phase was dried, filtered and evaporated to dryness. The resulting yellow oil was purified by chromatography to yield 6.45 g of a colourless oil.

NMR (CDCl$_3$) δ 7.80 (s, 1H), 7.38–6.83 (m, 4H), 6.4 (s, OH), 5.09 (t, 1H) 4.25 (t, 2H), 2.10–1.90 (m, 5H), 1.88–1.08 (m, 11H), 0.93 (d, 3H)

Example 6

(E)-3(2-Hydroxy-phenyl)-2-methyl-acrylic acid phenethyl ester

According to the same procedure of Example 3, (E)-3-(2-hydroxy-phenyl)-2-methyl-acrylic acid phenethyl ester was prepared from 3(2-hydroxy-phenyl)-2-methyl-acrylic acid, phenyl ethyl alcohol and p-toiuenesulfonic acid.

Example 7

3(4-Diethylamino-2-hydroxy-phenyl)-but-2-enoic acid ethyl ester

To a suspension of 5.27 g ethoxycarbonylmethylene-triphenylphosphorane in 10 ml of toluene, a solution of 2.02 g 1-(4-diethylamino-2-hydroxy-phenyl)-ethanone (DE 28 44 606) was dropped in at room temperature. Then the reaction mixture was heated to reflux. After refluxing for 31 hours the mixture was cooled down and evaporated to dryness. The resulting dark oil was purified by chromatography to yield a colourless oil.

NMR (CDCl$_3$) δ 7.22–7.09 (m, 1H), 6.57–6.4 2 (m, 1H), 6.32–6.20 (m, 2H), 5.01 (s, 1H), 4.18–4.01 (q, 2H), 3.42–3.24 (q, 4H), 2.49 (s, 3H), 1.31–1.08 (m, 9H).

The compounds of Examples 1–4 yield upon cleavage organoleptic coumarins, Examples 5 and 6 organoleptic coumarins and organoleptic alcohols and Example 7 a brightener coumarin.

Example 8

(E)-3-(2-Hydroxy-5-methyl-phenyl)-acrylic acid ethyl ester

A solution of 193.7 g 3-[5-methyl-2-(tetrahydro-pyran-2-yloxy)-phenyl]-acrylic acid ethyl ester (Bunce, R., Moore, J., Org. Prep. Proc., 29(3), 293 (1997)) and 2 g p-toluenesulfonic acid in 2.5 l of ethanol was stirred at room temperature for 24 hours. Then the reaction mixture was concentrated and the residue was diluted with ether, washed with saturated sodium bicarbonate and brine, dried and evaporated to dryness. The resulting yellow solid was recrystallized to yield 97.7 g of colourless crystals.

NMR (CDCl$_3$) δ 8.10–7.93 (d, 1H), 7.27 (s, 1H), 7.10–6.98 (d, 1H), 6.82–6.70 (d, 1H), 6.69–6.55 (d, 1H), 4.38–4.20 (q, 2H), 2.27 (s, 3H), 1.42–1.28 (t, 3H) ppm.

(E)-3-(2-Hydroxy-phenyl)-acrylic acid

To a solution of 100.0 g 3-(2-hydroxy-phenyl)-acrylic acid ethyl ester in 500 ml of ethanol, a solution of 50.9 g potassium hydroxide in 500 ml of water was dropped in at room temperature. After stirring at reflux for 28 hours, the reaction mixture was concentrated. The residue was diluted with 500 ml HCl 2N and extracted with ether. The organic phase was washed with 2N HCl and water, dried and evaporated to dryness. The resulting solid was recrystallized to yield 44.3 g of colourless crystals.

NMR (DMSO) δ 12.2 (br s, 1H), 10.2 (br s, 1H), 7.95–7.75 (d, 1H), 7.65–7.50 (d, 1H), 7.32–7.15 (m, 1H), 6.99–6.76 (m, 2H), 6.62–6.45 (d, 1H) ppm.

(E)-3-(2-Hydroxy-phenyl)-acrylic acid dec-9-enyl ester

A mixture of 5.0 g 3-(2-hydroxy-phenyl)-acrylic acid ethyl ester, 6.1 g dec-9-en-1-ol and 1.0 g tetraisopropyl-ortho-titanate was heated to 150° C. removing the ethanol formed. After stirring for 2.5 hours at this temperature, the reaction mixture was cooled, diluted with ether and washed with brine. The organic phase was dried and evaporated to dryness. The resulting oil was Kugelrohr-distilled, crystallized and recrystallized to yield 1.69 g of colourless crystals.

NMR (CDCl$_3$) δ 8.11–7.96 (d, 1H), 7.55–7.40 (d, 1H), 7.32–7.15 (m, 1H), 6.99–6.72 (m, 2H), 6.71–6.57 (d, 1H), 5.93–5.69 (m, 1H), 5.07–4.88 (m, 2H), 4.31–4.15 (t, 2H), 2.12–1.93 (m, 2H), 1.85–1.55 (m, 2H), 1.54–1.15 (m, 10H) ppm.

(E)-3-(2-Hydroxy-phenyl)-acrylic acid 2-ethyl-4-(2,2,3-trimethyl-cyclopent-3-enyl)-but-2-enyl ester According to the same procedure, 3-(2-hydroxy-phenyl)-acrylic acid 2-ethyl-4-(2,2,3-trimethyl-cyclopent-3-enyl)-but-2-enyl ester was prepared from 3-(2-hydroxy-phenyl)-acrylic acid ethyl ester, 2-ethyl-4(2,2,3-trimethyl cyclopentyl-3-en-1-yl)-but-2-en-1-ol and tetraisopropyl-o-titanate.

(E)-3-(2-Hydroxy-5-methyl-phenyl)-acrylic acid 2-ethyl-4-(2,2,3-trimethyl-cyclopent-3-enyl)-but-2-enyl ester According to the same procedure, 3-(2-hydroxy-5-methyl-phenyl)-acrylic acid 2-ethyl-4-(2,2,3-trimethyl-cyclopent-3-enyl)-but-2-enyl ester was prepared from 3-(2-hydroxy-5-methyl-phenyl)-acrylic acid ethyl ester, 2-ethyl-4(2,2,3-trimethyl cyclopentyl-3-en-1-yl)-but-2-en-1-ol and tetraisopropyl-o-titanate.

(E)-3(2-Hydroxy-5-methyl-phenyl)-acrylic acid 3-methyl-5-phenyl-pentyl ester

According to the same procedure, 3-(2-hydroxy-5-methyl-phenyl)-acrylic acid 3-methyl-5-phenyl-pentyl ester was prepared from 3-(2-hydroxy-5-methyl-phenyl)-acrylic acid ethyl ester, 3-methyl-5-phenyl-pentanol and tetraisopropyl-o-titanate.

(E)-3(4-Diethylamino-2-hydroxy-phenyl)-but-2-enoic acid dec-9-enyl ester

According to the same procedure, 3-(4-diethylamino-2-hydroxy-phenyl)-but-2-enoic acid dec-9-enyl ester was prepared from 3-(4-diethylamino-2-hydroxy-phenyl)-but-2-enoic acid ethyl ester, dec-9-en-1-ol and tetraisopropyl-o-titanate.

(E)-3-(4-Diethylamino-2-hydroxy-phenyl)-but-2-enoic acid 3-methyl-5-phenyl-pentyl ester According to the same procedure, 3-(4-diethylamino-2-hydroxy-phenyl)-but-2-enoic acid 3-methyl-5-phenyl-pentyl ester was prepared from 3-(4-diethylamino-2-hydroxy-phenyl)-but-2-enoic acid ethyl ester, 3-methyl-5-phenyl-pentanol and tetraisopropyl-o-titanate.

Example 9

3-[2-(tert-Butyl-dimethyl-silanyloxy)-phenyl]-acrylic acid tert-butyl-dimethyl-silyl ester To a solution of 5.0 g of (E)-3-(2-hydroxy-phenyl)-acrylic acid and 4.6 g of imidazole in 100 ml of DMF was added at room temperature a solution of 10.1 g of TBDMS-Cl. The reaction mixture was stirred overnight, poured onto 200 ml of cold water and extracted 3× with 150 ml of MTBE. The combined organic phases were dried (MgSO$_4$) and evaporated to dryness. The resulting oil was dried at 0.08 Torr/ 120–170° C. to remove excess of TBDMS-Cl to yield 11.4 g of 3-[2-(tert-butyl-dimethyl-silanyloxy)-phenyl]-acrylic acid tert-butyl-dimethyl-silyl ester as a yellowish oil.

NMR (CDCl$_3$) δ 7.96 (d, 1H), 7.52 (dd, IH), 7.23 (m, 1H), 6.94 (m, 1H), 6.82 (dd, 1H), 6.37 (d, 1H), 1.00 (s, 9H), 0.97 (s, 9H), 0.32 (s, 6H), 0.22 (s, 6H)

Example 10

3-[2-(tert-Butyl-dimethyl-silanyloxy)-phenyl]-acryloyl chloride

To a 0° C. cold solution of 6.3 g of 3-[2-(tert-Butyl-dimethyl-silanyloxy)-phenyl]-acrylic acid tert-butyl-dimethyl-silyl ester and 8 drops of DMF in 15 ml of CH$_2$Cl$_2$ was added dropwise 2.0 ml of oxalyl chloride. After complete addition the reaction mixture was allowed to warm to room temperature and stirring was continued for 60 h. The reaction mixture was filtered, evaporated to dryness and taken up in MTBE. The solution was cooled in the refrigerator overnight, filtered and evaporated to yield 4.4 g of 3-[2-(tert-Butyl-dimethyl-silanyloxy)-phenyl]-acryloyl chloride.

NMR (CDCl$_3$) δ 8.28 (d, 1H), 7.55 (dd, 1H), 7.35 (m, 1H), 7.01 (m, 1H), 6.87 (dd, 1H), 6.63 (d, 1H), 1.04 (s, 9H), 0.26 (s, 6H)

Example 11

3-(2-Hydroxy-phenyl)-acrylic acid 3-(3-isopropyl-phenyl)-but-1-enyl ester

To a suspension of 0.72 g of NaH (55% in oil), previously washed with hexane, in 22.5 ml of THF was added 1.67 ml of tert-butanol over a period of 12 min. The reaction mixture was stirred at room temperature for 1.25 h, was then cooled to −15° C. and 2.85 g of 3-(3-isopropyl-phenyl)-butanal (Florhydral) was slowly added. Stirring was continued for 45 min. and then this cold enolate solution was added via Teflon canula to a −5° C. cold solution of 4.44 g of 3-[2-(tert-butyl-dimethyl-silanyloxy)-phenyl]-acryloyl chloride in 7.5 ml of THF. After complete addition stirring at −5° C. was continued for 1 h, the reaction mixture was quenched with 80 ml of water/40 ml of brine and was extracted with MTBE. The combined organic phases were washed with water/brine 2:1, dried ($MgSO_4$) and evaporated to dryness to yield 6.65 g of crude 3-[2-(tert-Butyl-dimethyl-silanyloxy)-phenyl]-acrylic acid 3-(3-isopropyl-phenyl)-but-1-enyl ester as a yellowish, viscous oil.

To a 0° C. cold solution of 6.2 g of this oil in 70 ml of THF was added slowly 13.7 ml of a 1M TBAF/THF solution. The reaction mixture was stirred at 0° C. for 1.5 h, poured onto 200 ml of $H_2O$ and extracted 3× with 150 ml of MTBE. The combined organic phases were washed with brine, dried ($MgSO_4$) and evaporated to dryness. The resulting oil was purified by chromatography to yield 2.64 g of 3-(2-Hydroxy-phenyl)-acrylic acid 3-(3-isopropyl-phenyl)-but-1-enyl ester in form of a yellowish oil.

NMR ($CDCl_3$) δ 8.12 and 8.01 (d, 1H), 7.50–6.80 (m, 10H), 6.66 and 6.56 (d, 1H), 5.75 and 5.13 (m, 1H), 4.13 (m, CH), 3.53 (m, CH), 2.89 (m, CH), 1.42 (d, 3H), 1.25 (d, 6H)

Example 12

(E)-3-[2(tert-Butyl-dimethyl-silanoxy)-phenyl]-acrylic acid

To a solution of 8.2 g of (E)-3-(2-hydroxy-phenyl)-acrylic acid and 15.2 g of TBDMS-Cl in 10 ml of DMF was added 11.9 g of imidazole and the mixture was stirred at room temperature for 24 h. After aqueous work-up, the bis-silylated product was saponified with 2.1 g of LiOH in THF-$H_2O$ for 0.5 h at 0° C. The mixture was concentrated in vacuo and TBDMS-OH removed by extraction with hexane. The aqueous layer was acidified to pH 4 with $KHSO_4$ and extracted with EtOAc. The organic phases were washed with brine, dried ($Na_2SO_4$) and evaporated to dryness. The semi-solid residue was suspended in hexane, filtered and the filtrate evaporated to dryness to yield 7.5 g of a pale yellow oil, which solidified upon standing.

NMR ($CDCl_3$) δ 8.08 (d, 1H), 7.46 (dd, 1H), 7.18 (dt, 1H), 6.87 (t, 1H), 6.75 (dd, 1H), 6.31 (d, 1H), 0.93 (s, 9H), 0.13 (s, 6H)

Example 13

(E)-3-(2-Hydroxy-phenyl)-acrylic acid 1-ethoxy-3-(3-isopropyl-phenyl)-butyl ester A solution of 6.5 g of (E)-3-[2-(tert-Butyl-dimethyl-silanoxy)-phenyl]-acrylic acid and 5.5 g of 1-(3-ethoxy-1-methyl-allyl)-3-isopropyl-benzene, accessible from 3-(3-isopropyl-phenyl)-butyraldehyde via a two step procedure according to P. D. Bartlett and A. A. Frimer, Heterocycles 11, 419–435, (1978), in 25 ml of toluene was heated to reflux and stirred for 16 h. After concentration, the reaction mixture was purified by flash chromatography to yield 7.5 g of the intermediate (E)-3-[2-(tert-Butyl-dimethyl-silanoxy)-phenyl]-acrylic acid 1-ethoxy-3-(3-isopropyl-phenyl)-butyl ester as a pale yellow oil. This was dissolved in 50 ml THF and treated at 0° C. with 4.7 g of TBAF.$3H_2O$. After 20 min., the mixture was concentrated and purification by flash chromatography yielded 2.2 g of the title ester (a mixture of diastereoisomers) as a pale yellow oil.

NMR ($CDCl_3$) d 8.12 and 8.08 (d, 1H), 7.47 (dt, 1H), 7.35 (br s, 1H), 7.31–7.18 (m, 2H), 7.12–6.98 (m, 3H), 6.92 (dt, 1H), 6.83 (dd, 1H), 6.68 and 6.61 (d, 1H), 5.96 and 5.77 (dd, 1H), 3.82–3.65 (m, 1H), 3.63–3.40 (m, 1H), 3.05–2.77 (m, 2H), 2.22–1.95 (m, 2H) and 1.38–1.12 (m, 12H)

Example 14

(E)-3(2-Hydroxy-phenyl)-acrylic acid 3(4-tert-butyl-phenyl)-1-ethoxy-propyl ester A solution of 3.1 g of (E)-3-[2-(tert-Butyl-dimethyl-silanoxy)-phenyl]-acrylic acid, 3.0 g of 1-tert-butyl-4-(3-ethoxy-2-methyl-allyl)-benzene, accessible from 3-(4-tert-butyl-phenyl)-2-methyl-propionaldehyde via a two step procedure according to P. D. Bartlett and A. A. Frimer, Heterocycles 11, 419–435, (1978), and 20 mg of p-TSA in 25 ml of toluene was stirred at 0° C. for 4 h and at room temperature for 14 h. The reaction mixture was partitioned between saturated sodium carbonate and hexane and the organic layer was washed with brine, dried over ($Na_2SO_4$) and evaporated to dryness to yield 5.3 g of the crude intermediate (E)-3-[2-(tert-Butyl-dimethyl-silanoxy)-phenyl]-acrylic acid 3-(4-tert-butyl-phenyl)-1-ethoxy-propyl ester as a pale yellow oil. This was dissolved in 20 ml of THF and treated at 0° C. with 3.2 g of solid TBAF-$3H_2O$. After 30 min., the mixture was concentrated and purification by repeated flash chromatography yielded 1.2 g of the title ester (a mixture of diastereoisomers) as a pale yellow oil.

NMR ($CDCl_3$) d 8.17 and 8.13 (d, 1H), 7.50 (ddd, 1H), 7.36–7.18 (m, 4H), 7.11 (br dd, 2H), 6.98–6.83 (m, 2H), 6.73 and 6.69 (d, 1H), 5.94 (t, 1H), 3.92–3.70 (m, 1H), 3.71–3.54 (m, 1H), 3.05–2.81 (m, 1H), 2.52–2.34 (m, 1H), 2.30–2.12 (m, 1H) and 1.31 (s, 9H), 1.33–1.20 (m, 3H), 0.97 and 0.90 (t, 3H)

Example 15

Test cloth was washed with detergent to which one or more of the precursors of Examples 1–14 had been added. The cloth was then line dried. The cloth dried in sunlight had a distinct fragrance note, as determined by a trained panel. In contrast, the cloth dried without sunlight was olfactively neutral.

Example 16

Test cloth was washed with a detergent and then a fabric softener, containing one ore more of the precursors of Examples 1–14, was added to the rinse cycle. The cloth was then line dried. The cloth dried in sunlight had a distinct fragrance note, as determined by a trained panel. In contrast, the cloth dried without sunlight was olfactively neutral.

Example 17

A 1% solution of one or more of the products of Examples 1–14 in ethanol was applied to cigarette papers to produce levels of 5–50,000 ppm of each flavorant. The paper was incorporated in cigarettes and, upon burning, released a fragrant odor.

Example 18

A broad spectrum (UV-A and UV-B) oil/water sunscreen lotion was prepared with 0,5%.

| Recipe:% | Compound | Chemical Name |
|---|---|---|
| Part A | | |
| 2% | PARSOL MCX | Octyl methoxycinnamate |
| 3% | PARSOL 1789 | 4-4-Butyl-4'methoxy-dibenzoyl methane |
| 12% | Cetiol LC | Coco-caprylate/caprate |
| 4% | Dermol 185 | Isostearyl neopentanoate |
| 0,25% | Diethyl- | PEG-2-stearate eneglycol monostearate |
| 1% | Cetylalcohol | Cetylalcohol |
| 0,25% | MPOB/PPOB | Methyl-propylparabene |
| 0,1% | EDTA BD | EDTA-sodium salt |
| 1% | Amphisol DEA (Giv.) | Diethanolamine cetyl-phosphate |
| Part B | | |
| 20% | Permulene TR-1 (+%) | Acrylate C10–C30 Alkyl-acrylate |
| 50,1% | water deion | water deion |
| 5% | Propyleneglycol | 1,2-Propanediol |
| 0,8% | KOH (10%) | Potassium hydroxide |

Part A was heated in a reactor to 85° C. Part B was slowly added within 10 min., followed by addition of KOH and 0.5% of the product of Example 5. The emulsion was then cooled and degassed.

The invention being thus described, it will be obvious that the same may be varied in many ways. Such variations are not to be regarded as a departure from the spirit and scope of the invention and all such modifications are intended to be included within the scope of the following claims.

What is claimed is:

1. A compound of Formula I

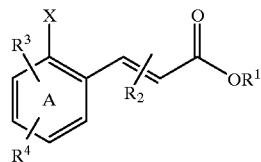

wherein

A is selected from benzene and naphthalene rings;

$R^1$ is a saturated, unsaturated, straight, branched, alicyclic or an aromatic $C_{10}$–$C_{30}$ hydrocarbon residue which can contain heteroatoms and can be substituted by an ionic substituent;

$R^2$ in 2- or 3-position is a hydrogen, a straight or branched $C_1$–$C_6$ residue, an optionally substituted aromatic or an optionally substituted heterocyclic residue;

$R^3$ and $R^4$ are a hydrogen, a straight or branched $C_1$–$C_6$ alkyl, a $C_1$–$C_6$ alkoxy residue, a substituted or condensed heterocyclic residue, —OH, —$NO_2$, —$NH_2$, —N($C_1$–$C_6$ alkyl)$_2$, —N(hydroxyalkyl)$_2$, —$NHCO_2CH_3$ or —NH(heterocycle), wherein $R^2$, $R^3$ and $R^4$ are the same or different;

X is an —OH or $NHR^6$, wherein $R^6$ is a hydrogen, a saturated or unsaturated, straight or branched $C_1$–$C_{20}$ hydrocarbon, or an optionally substituted aromatic or heterocyclic residue;

and the acrylic double bond is of the E configuration.

2. A compound according to claim 1 wherein $R^1$ is a saturated, unsaturated, straight or branched $C_{10}$–$C_{30}$ hydrocarbon residue comprising one or more O atoms, N atoms, C(O) groups, alkoxy groups and mixtures thereof.

3. A compound according to claim 1 wherein $R^1$ is a saturated, unsaturated, straight or branched $C_{10}$–$C_{30}$ hydrocarbon residue substituted by an ionic substituent of Formula $NR^5_3{}^+$, wherein $R^5$ is a residue of a fatty acid or an alkyl group with 1 to 30 carbon atoms.

4. A compound according to claim 1 wherein $R^2$ is a heterocyclic residue of Formula

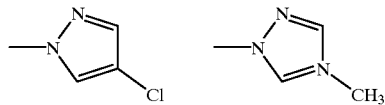

5. A compound according to claim 1 wherein at least one of $R^3$ and $R^4$ is a five membered heterocyclic residue comprising N atoms and/or O atoms.

6. A compound according to claim 1 wherein at least one of $R^3$ and/or $R^4$ is a hydrogen, —N($C_1$–$C_6$ alkyl)$_2$, —$NH_2$, or a five membered heterocyclic residue, substituted by $C_1$–$C_6$ aliphatic and/or aromatic substituents.

7. A compound according to claim 1 wherein $R^2$ is hydrogen or methyl.

8. A compound according to claim 1 wherein $R^1$ is a residue of an olfactory alcohol of Formula $R^1OH$.

9. A compound according to claim 1 wherein $R^1$ is a residue of the enol form of an olfactory aldehyde of Formula $R^1HO$.

10. A compound according to claim 1 wherein $R^1$ is a residue of the enol form of an olfactory ketone of Formula $R^1O$.

11. A compound according to claim 1 wherein $R^1$ is a substituted alkyl, an alkenyl or an arylalkyl residue carrying a 1-alkoxy, 1-aryloxy or 1-arylalkoxy residue.

12. A compound according to claim 1 wherein a residue of Formula Ia:

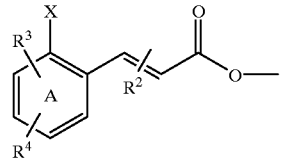

is a precursor for a fragrant coumarin.

13. A compound according to claim 1 wherein a residue of Formula Ia

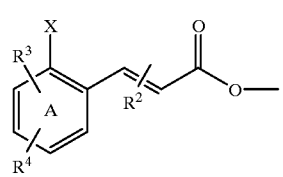

is a precursor for a fluorescent whitening coumarin.

14. A compound according to claim 12 wherein $R^1$ is a residue of an olfactory alcohol, an aldehyde or ketone and the residue of Formula Ia

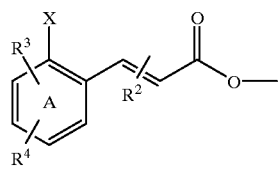

is a precursor for a fragrant coumarin.

15. A method for preparing compositions which provide upon activation organoleptic, antimicrobial or fluorescent whitening properties comprising incorporating into one of these compositions a compound of Formula I:

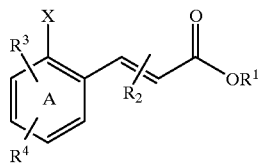

(I)

wherein

A is selected from benzene and naphthalene rings;

$R^1$ is a saturated, unsaturated, straight, branched, alicyclic or an aromatic $C_{10}$–$C_{30}$ hydrocarbon residue which can contain heteroatoms and can be substituted by an ionic substituent;

$R^2$ in the 2- or 3-position is a hydrogen, a straight or branched $C_1$–$C_6$ residue, an optionally substituted aromatic or an optionally substituted heterocyclic residue;

$R^3$ and $R^4$ are a hydrogen, a straight or branched $C_1$–$C_6$ alkyl, a $C_1$–$C_6$ alkoxy residue, a substituted or condensed heterocyclic residue, —OH, —$NO_2$, —$NH_2$, —N($C_1$–$C_6$ alkyl)$_2$, —N (hydroxyalkyl)$_2$, —$NHCO_2CH_3$ or —NH (heterocycle);

wherein $R^2$, $R^3$ and $R^4$ are the same or different;

X is an —OH or $NHR^6$, wherein $R^6$ is a hydrogen, a saturated or unsaturated, straight or branched $C_1$–$C_{20}$ hydrocarbon, or an optionally substituted aromatic or heterocyclic residue; and the acrylic double bond is of the E configuration.

16. A method according to claim 15 wherein the precursors are incorporated into laundry products.

17. A method according to claim 15 wherein the precursors are incorporated into tobacco products.

18. A method according to claim 15 wherein the precursors are incorporated into cosmetics and toiletries.

* * * * *